United States Patent
Volker

(10) Patent No.: US 10,159,939 B2
(45) Date of Patent: Dec. 25, 2018

(54) REVERSE OSMOSIS SYSTEM

(71) Applicant: Manfred Volker, Blankenbach (DE)

(72) Inventor: Manfred Volker, Blankenbach (DE)

(73) Assignee: Vivonic GmbH, Sailauf (DE)

( * ) Notice: Subject to any disclaimer, the term of this patent is extended or adjusted under 35 U.S.C. 154(b) by 88 days.

(21) Appl. No.: 14/638,343

(22) Filed: Mar. 4, 2015

(65) Prior Publication Data

US 2015/0231571 A1    Aug. 20, 2015

Related U.S. Application Data

(63) Continuation-in-part of application No. 13/466,697, filed on May 8, 2012.

(30) Foreign Application Priority Data

May 27, 2011    (DE) .................. 10 2011 102 662

(51) Int. Cl.
*B01D 65/02*    (2006.01)
*C02F 1/44*    (2006.01)

(52) U.S. Cl.
CPC .......... *B01D 65/02* (2013.01); *B01D 65/022* (2013.01); *C02F 1/441* (2013.01); *B01D 2321/08* (2013.01); *B01D 2321/32* (2013.01)

(58) Field of Classification Search
CPC .......... B01D 2321/32; B01D 2311/103; B01D 2321/08; B01D 2321/40; B01D 65/022; B01D 65/027; B01D 61/025; C02F 1/441
See application file for complete search history.

(56) References Cited

U.S. PATENT DOCUMENTS 3,417,870 A    12/1968    Bray
3,598,731 A    8/1971    Frykhult et al.
(Continued)

FOREIGN PATENT DOCUMENTS

DE    10262036 A1    6/2004
DE    10319196 A1    7/2004
(Continued)

OTHER PUBLICATIONS

German Language Wikipedia: Umkehrosmose. Retrieved Jun. 26, 2012. Last Updated Jun. 20, 2012.
(Continued)

*Primary Examiner* — Terry K Cecil
(74) *Attorney, Agent, or Firm* — Greer, Burns & Crain, Ltd.

(57) ABSTRACT

A method is provided for sanitizing a reverse osmosis system to supply high-purity permeate. Included in the method is supplying raw water to a feed tank and to a filter module using a raw-water inlet line having an inlet valve. A primary circuit is provided, and has a first pump connected to the filter module. A secondary circuit is provided, and has a second pump and a heater, both of which are connected to the filter module. The primary circuit is separated from the secondary circuit using a semipermeable membrane disposed in the filter module. The secondary circuit of the reverse osmosis system is cleaned or disinfected while the raw-water inlet line is in a disconnected state and the inlet valve is in a closed state using the second pump and the heater.

12 Claims, 3 Drawing Sheets

(56) References Cited

U.S. PATENT DOCUMENTS

| | | | |
|---|---|---|---|
| 4,419,206 A | 12/1983 | Frame | |
| 6,908,546 B2 | 6/2005 | Smith | |
| 8,784,662 B2 | 7/2014 | Becker et al. | |
| 8,808,537 B1 * | 8/2014 | Livingston | C02F 9/005 |
| | | | 210/196 |
| 2005/0121388 A1 | 6/2005 | Wood et al. | |
| 2009/0134080 A1 * | 5/2009 | Fabig | B01D 61/022 |
| | | | 210/137 |

FOREIGN PATENT DOCUMENTS

| | | |
|---|---|---|
| DE | 10319221 A1 | 7/2004 |
| DE | 102008036899 A1 | 2/2010 |
| DE | 102009057562 A1 | 6/2011 |
| EP | 1440041 B1 | 7/2004 |
| JP | 02035916 | 2/1990 |
| JP | 02227128 | 9/1990 |

OTHER PUBLICATIONS

Corresponding parent U.S. Appl. No. 13/466,697, filed May 8, 2012.
U.S. Non-Final Office Action from Parent U.S. Appl. No. 13/466,697, dated May 18, 2017.

* cited by examiner

REVERSE OSMOSIS SYSTEM

CROSS-REFERENCE

The present application is a Continuation-In-Part application of U.S. patent application Ser. No. 13/466,697 filed May 8, 2012, which is incorporated herein by reference, which claims priority to German Patent Application No. 10 2011 102 662.6 filed May 27, 2011.

The present invention refers to a device for water treatment according to the reverse osmosis principle. Devices of such types, reverse osmosis systems, are particularly used in combination with hemodialysis devices to obtain sterile high-purity water from tap water for preparing the dialysis liquid.

The present invention particularly aims at a liquid that is as sterile as possible.

This object is achieved by a reverse osmosis system which can be coupled with at least one consumer, particularly a dialysis device, to supply the consumer with high-purity permeate, comprising a raw-water inlet line which supplies raw water to a filter module the primary circuit of which is separated by a semipermeable membrane from a secondary circuit which comprises a permeate collection tube which is connected at one end to a distribution system for permeate which comprises a permeate inlet line with at least one connection to which a consumer can be coupled, and a permeate return line. The permeate distribution system comprises at least one device for cleaning and/or disinfection. A concentrate outlet line leads away from the primary circuit of the filter module. The permeate collection tube, the cleaning and/or disinfection device and a circulation pump are arranged in a circulation circuit.

In one embodiment, a method is provided for sanitizing a reverse osmosis system to supply high-purity permeate. Included in the method is supplying raw water to a feed tank and to a filter module using a raw-water inlet line having an inlet valve. A primary circuit is provided, and has a first pump connected to the filter module. A secondary circuit is provided, and has a second pump and a heater, both of which are connected to the filter module. The primary circuit is separated from the secondary circuit using a semipermeable membrane disposed in the filter module. The secondary circuit of the reverse osmosis system is cleaned or disinfected while the raw-water inlet line is in a disconnected state and the inlet valve is in a closed state using the second pump and the heater.

Further details and configurations of the invention become apparent from the following description of embodiments taken in conjunction with the figures, of which:

DETAILED DESCRIPTION OF THE DRAWINGS

As is generally known, the functional principle of reverse osmosis systems consists in that the water to be treated is guided in a filter module under high pressure along the surface of a semipermeable membrane, with part of the water, the so-called permeate, being guided over the surface of the spirally wound membrane in such a manner that it exits through the membrane and is collected at the other side of the membrane within the module in a permeate collecting tube and is supplied from there via hydraulic connections to the points of consumption.

The part of the raw water that does not pass through the membrane and is enriched with retained substances, the so-called concentrate, flows at the end of the flow section out of the filter module.

Figure 1:
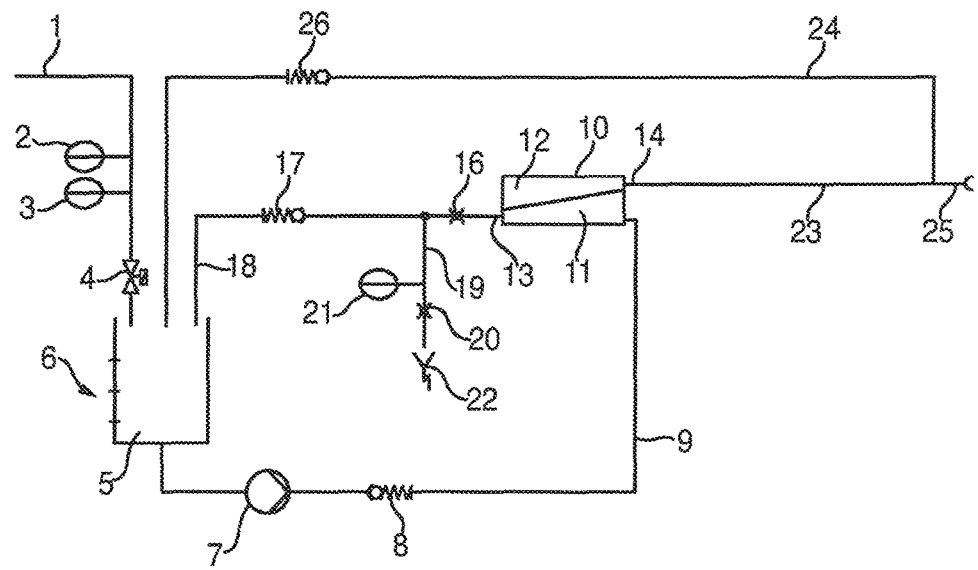
FIG. 1 shows the scheme of a typical reverse-osmosis system according to the prior art.

The scheme shown in FIG. 1 illustrates, as a typical example, the cooperation of essential functional elements of a reverse osmosis system according to the prior art. The raw water to be treated flows out of the feeding line 1 and via the valve 4 into a buffer vessel 5 with installed fill level control 6. The water passes out of this container 5 through the line 9 via the pump 7 into the filter module 10, the primary circuit 11 of which is separated by the semipermeable membrane 49 from the secondary circuit 12. The permeate flows out of the secondary circuit 12 into a ring line 23/24 from which the consumer lines 25 divert. Permeate produced in excess can flow back at the end of the ring line 23/24 via an inserted pressure-maintaining valve 26 into the vessel 5, the setting of said valve determining the pressure prevailing in the ring line 23/24.

The pressure needed for filtration in the primary circuit 11 of the filter module 10 is produced by the pump 7 in combination with a flow resistance means 16 which is inserted into the concentrate line 13 downstream of the filter, e.g. in the form of a throttle valve or a pressure valve.

Reverse osmoses particularly also serve the recovery of sterile water.

The part of the supplied tap water that does not pass through the filter membrane 49 and is enriched with retained chemical water substances and with bacteria forms a biofilm on the inner surfaces of the liquid-conducting system.

The deposits of the biofilm in the primary circuit 11 can pass through the non-ideal filter membrane 49 as pyrogens and endotoxins and contaminate the high-purity permeate side 12/23/24.

These parts will deposit there as a biofilm and contaminate the permeate.

For the purpose of simplification the term cleaning is chosen hereinafter for the description of the decontamination, disinfection and purification measures.

One reason for the bacterial enrichment of the permeate must also be seen in the permeate collection tube area through which no or only a moderate flow is passing. This line section of the high-purity secondary side can only be thermally or chemically disinfected and cleaned under great efforts.

Constructionally, the filter membrane of the reverse osmosis module is spirally wound around a permeate collection tube. Part of the liquid is here supplied from the primary side to the secondary side through the membrane to the permeate collection tube and fed from said place to the consumer.

The reason for the bacterial enrichment in the permeate collection tube is on the one hand the restricted, relatively small transmembranic flow through the filter membrane to the permeate collection tube, and on the other hand the cleaning process for the permeate collection tube always presupposes a transmembranic cleaning operation, i.e. a cleaning of the primary side, and thus of the total system, and this operation is cost- and time-intensive.

However even if the secondary-side distribution system is cleaned, there is the problem that one cannot guarantee absolute sterility, especially on the basis of normative guidelines, because a re-contamination from the permeate collection tube is very likely.

Another reason for re-contamination is that with the known applications the bacterial growth within the secondary-side distribution system can only be prevented up to the transfer point to the consumer by means of cleaning measures.

For instance in dialysis devices with a free inlet according to EN 1717 one does not take into account the path leading from the transfer point of the ultrapure water line of the reverse osmosis system up to the free inlet of the dialysis device.

Likewise, when permeate is stored e.g. in ultrapure water tanks or bags, the filling line is not fully included in the disinfecting process. This problem is also applicable to mixing facilities for producing medicinal solutions on the one hand from powdery, paste-like, granulated or other highly concentrated raw materials and on the other hand from high-purity permeate on condition that these systems also contain a permeate storage means with feed lines for the permeate or the permeate production.

To keep this route sterile, considerable resources in the form of electrical energy during hot cleaning or also of chemical disinfectants and of the manpower hired would be needed because it is normally not only the secondary distribution system, but also the RO system and the connected consumer, e.g. the dialysis device, that have to be integrated into the disinfecting process.

Apart from the contamination of the waste waters, especially the input of large amounts of chemical disinfectants poses considerable safety risks for patients because the slightest amounts or residues in the device or in the conduits may have toxic impacts on patients. Such impacts can only be prevented by way of large flushing volumes and a careful control as to residues.

As a rule, the disinfecting measures are therefore limited to the respectively connected devices; the interfaces and the ultrapure water transfer points, respectively, are not taken into consideration.

Exceptions are here integrated hot-cleaning operations in the case of which great amounts of hot water are prepared and e.g. supplied to dialysis devices and conveyed therethrough to the outlet.

The aim is to ensure absolute sterility of the high-purity distributor circuit including the connected consumer line and, nevertheless, to reduce the operating costs for hygienic measures.

A fully automatic purification is here needed without any risk for patient and user and without carrying out, as is presently superfluously done, the disinfection of the reverse osmosis system and the connected consumers with chemicals in an imperative way.

It should here be the objective to achieve the lowest possible energy input and no negative impact on the waste waters by chemicals or thermal energy.

The aim should be a partial disinfection of the whole high-purity distribution system, i.e. the secondary side, also within the connected consumer in dialysis devices up to the water inlet, i.e. the supply tank. Different cleaning methods at the primary and secondary side of the membrane can be carried out. A complete integrated cleaning of the whole system is here also possible.

A measuring option for measuring the extent of the soiling/contamination degree and a resulting warning or the automatic introduction of a cleaning operation, respectively, are needed.

Control as to the absence of disinfectants shall not be required.

Gentle cleaning methods should be chosen to prevent any restriction of the service lives of the components used, particularly the filter membrane.

According to the invention the permeate collection tube of the membrane is included in the cleaning of the high-purity secondary permeate distribution.

The module of the reverse osmosis system is here operated preferably as a 4-pole module, resulting in a closed secondary circuit with minimal dead spaces that is to be cleaned independently of the primary circuit of the reverse osmosis system.

With great advantage a further pump is used for this in the secondary circuit. Primary side and secondary side have thereby to be cleaned independently of one another by means of different cleaning methods and intervals.

With advantage the invention provides a cleaning method in which ozonization of the secondary distribution system takes place. This can also take place in alternation with a hot cleaning of the reverse osmosis system or also of the total system. Chemical cleaning or a combination of thermal and chemical cleaning is here not explicitly ruled out.

It has also been found that the combination of least dosed ozone and increased temperature in the water only causes minimal damage to material because oxidation and decomposition processes of the ozone are accelerated. As a consequence, this method also permits an ozonization of the reverse-osmosis primary side and thus of the membrane.

Likewise, an ozone input into a possibly connected storage container e.g. in a mixing system in communication with the reverse osmosis system, makes sense in order to keep the permeate-prepared solution microbiologically stable.

With great advantage, apart from the water inlet valve of the consumer, a further valve is connected to the outlet particularly in dialysis devices. This further valve passes the cleaning agent during cleaning up to the inlet valve of the connected consumer. Without the operation of the consumer the interface from the distribution system of the reverse osmosis system to the dialysis-device water inlet can thereby be cleaned almost without any dead spaces.

With advantage the invention provides for a cleaning chamber in the primary circulation circuit of the reverse osmosis system, the design of which allows and provides for an electrical or magnetic or electromagnetic or electrolytic or sonographic effect or a combination of different physical effects of the liquid flowing therethrough.

It is the function of the cleaning chamber to prevent, on the one hand, any decontamination by the microorganisms and on the other hand the stabilization of the hardeners, so that deposits on the reverse osmosis membrane are prevented.

Use and place of installation of the cleaning chamber are however not restricted to the described function.

Since the disinfection action of the electrolytically produced oxygen radicals as well as the stabilization of the lime crystals in the liquid are only temporary after the cleaning chamber has been switched off, the high-pressure throttle is advantageously opened periodically and/or at the end of an operating cycle either by motor or, if a fixed flow-resistance means is installed, by means of a bypass valve with discharge valve. This suddenly increases the flow in the primary circulation circuit and the surfaces of the liquid-conducting components are flooded and flushed.

Since the effect of the cleaning chamber cannot be determined by the user directly through its physical effect or its effects on crystal formation, a cleaning sensor is provided with great advantage for the primary circuit.

Components or liquid-conducting lines can here be configured with transparent or translucent material to check the contamination visually or opto-electronically.

In an advantageous configuration the associated transmitter/receiver unit is arranged in one plane. The optical transmitter signal is here projected onto an opposite reflecting surface and is reflected from there to the optical receiver.

The preferred solution is a transparent tube section with opposite transmitter/receiver sensors. The quantity of the receiver signal is here a direct function of the degree of soiling.

With great advantage, in order to improve the impact in time and to enhance the physical cleaning effects, an additional circulation pump can be connected with a cleaning chamber between the concentrate outlet and the mixed water inlet. This may be an additional cleaning chamber with a different physical effect with respect to the cleaning chamber. The flow through the primary circuit in the sense of an optimal overflowing of the membrane 49 is here ensured, namely substantially independently of the action of the pump 7 used for mixed-water supply, pressure build-up and circulation performance.

To remove substance residues, another inventive feature is that the liquid of the primary circulation circuit is conveyed by way of a tangential inlet through a cylindrical centrifugal chamber on the upper end of which a turbine blade, which is rotatable by liquid pressure, conveys the substances and particles to be separated downwards and passes the cleaned liquid through a hollow shaft or a strainer-like cylinder upwards.

A collection chamber for the particles or lime clusters to be precipitated is located under the centrifugal chamber. The discharge valve 26 may be secured to the collection chamber if a centrifugal chamber is present. The centrifugal chamber may here also be arranged upstream of the primary circuit for instance in front of the supply tank (5).

With great advantage it is also suggested that the power output stages for the control of the cleaning chamber should be configured such that they are adjustable with respect to frequency and current and should be controlled and monitored for malfunction by the processor of the reverse osmosis system. A specific bit pattern can here be output as a test signal and monitored by means of a watch dog. The respective operating status and also the signal shape are here displayed via the display device of the reverse osmosis system and stored with memory modules.

The data can be requested at any time by means of an interface e.g. Ethernet connection of the microcontroller of the reverse osmosis system.

Figure 2:
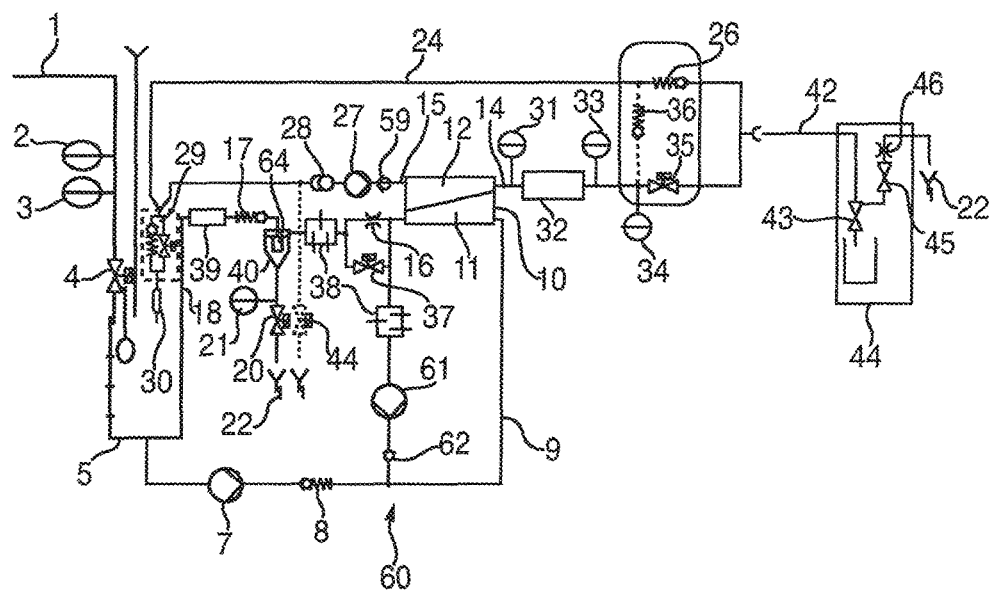
FIG. 2 shows the scheme of a comparable reverse-osmosis system with equipment features according to the invention.

FIG. 2 shows the module (10) with the mixed-water inlet (9), the concentrate outlet (13), the permeate supply (14) and the permeate circulation line (15). The membrane primary circuit (11) is here operated via the pump (7), the high-pressure throttle (16), the cleaning chamber (38) and the centrifugal chamber (40) via the pressure maintaining valve (17) and the heater (39) in such a manner that a sufficiently high transmembrane pressure is created for conveying the liquid of the primary circuit (11) into the membrane secondary circuit (12). Due to the high transmembrane pressure the liquid of the membrane secondary circuit (12) (permeate) is passed over the temperature sensors (31/33), the heater (32), the conductivity cell (34) and the valve (35) via the line (42) to the consumer (44). The pump (27) must here be operated in a selective way.

In the unconnected state of the consumer (44) the liquid can be returned either via the lines (23/24) or, in the connected state of the valve, via the permeate-ring safety valve (36) to the supply tank (5).

For cleaning the high-purity secondary circuit (12/23/24/48) the pump (27) is circulating the liquid via the heater (32) during thermal cleaning until a microbiologically inactivating temperature has been reached.

When the secondary circuit is cleaned by means of the electrolytic ozone cell (28), said cell is switched on via a safety circuit and the ozone/liquid mixture is circulated in a circuit by means of pump (27) for such a long time until a microbiologically inactivating effect has been achieved.

The primary circuit (11/9/18) can here be deactivated with the pump (7) so that a purification of the high-purity circuit (12/23/24) is exclusively carried out.

Position and mode of operation of the pump (27) and of the ozone cell (28) are not limited to the method described.

In the event that an integrated disinfecting operation, i.e. with coupled and operated consumer (44), is carried out, the consumer can be supplied with hot water or ozone via the opened valve (43). A disinfection of the line (42) is also possible via the opened valve (45) without operation of the consumer (44) to the drainage (22). The throttle valve (46) reduces the volume flow. The switching of the consumer valves (43/45) or the communication between consumer (44) and RO system (60) is here carried out via the communication interfaces of the RO (60) or of the consumer (44). The commands can here be given by the RO (60) to the consumer (44) and also inversely.

Valve (29) is opened for the hot cleaning of the whole RO system (60) without consumer (44). The pump (7) feeds the liquid circuit such that enough permeate flows via the heater (32). Valve (37) can here be opened. The pump (27) performs a circulatory supportive operation in the secondary circuit (23/24/48). The heated permeate flows selectively via the valves (26/35) or (36) back to the supply tank (5) until a microbiologically inactivating status has been reached.

It is also possible to feed ozone in small amounts into the primary circuit (9/18) to achieve a disinfecting action without oxidation of the membrane material there. In combination with the ozone input the heater (32) can be operated such that only a short-term ozonization that is gentle on the material is carried out.

Apart from the hot cleaning of the whole reverse osmosis system, it is also possible to clean the liquid of the primary circuit permanently by means of the cleaning chamber (38). To this end the liquid is passed with the pump (7) running via the cleaning chamber (38) and the centrifugal chamber (40). Part of the circulating liquid is passed via the concentrate flow meter (21) and the concentrate discharge valve (30) to the outlet.

To flush out substance residues, the high-pressure bypass valve (37) is cyclically opened and the substance residues contained in the primary circuit are flushed out to the drainage (22) via the opened valve (20).

Optionally, the primary circuit is cleaned via the pump (61) and via a cleaning chamber (38) which is either arranged in addition or is operated alone.

With the methods described, both primary and secondary circuits of the reverse osmosis system and of the distributor circuit can be cleaned with different methods and independently of one another in a cost-saving and efficient manner.

Hot cleaning of the secondary circuit (14, 15, 24) can be carried out with great advantage in the closed state of the water inlet valve (4) and in the disconnected state of line (1), respectively.

Especially with spatially confined applications, e.g. in intensive care units, the RO system (60) can be completely separated from the water network during long periods of non-use and can be parked without any water connection at another place.

While being just electrically powered at a socket, the RO system (60) is cleaned at a high hygienic level for a long period of time so that before a sudden specific operation there will be no delay times because of flushing or disinfecting processes.

To this end, pump (27) is switched on by way of an independently running preselectable program with fixed intervals and running times, and the whole secondary circuit (14, 15, 24) of high-purity permeate is heated via the switched-on heater (32) to a necessary disinfecting temperature.

Pump (7) is here expediently circulating the primary circuit (11, 9, 18) via feed tank (5). Valve (37) is opened for this purpose to achieve only a moderate pressure in the secondary circuit on the one hand and to obtain a high flow velocity in the primary circuit on the other hand.

The aforementioned hot cleaning phase is carried out without any water consumption by a consumer and without any water waste, so that the whole RO system can be hygienically kept available all the time while being just operated by electric power.

Furthermore, pump (7) can cause a high flow velocity in the primary circuit and can flush the membrane from deposits of a biofilm on the primary side of the membrane so that no pyrogens, endotoxins etc. can pass the membrane to the secondary side.

In this way, the RO system can be hygienically kept available all the time while being just operated by electric power. This is an important aspect of the present invention.

Figure 2A:
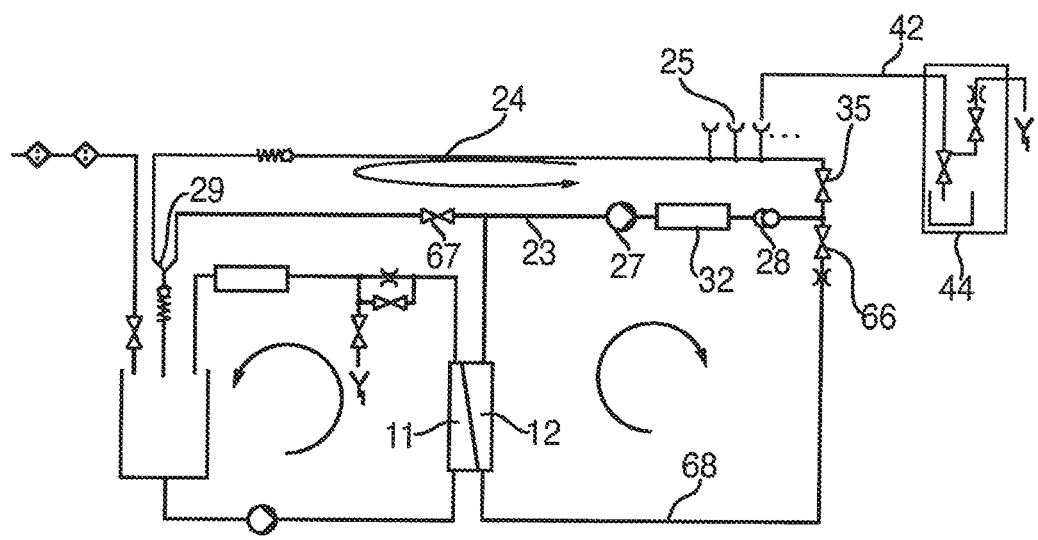
FIG. 2A shows an alternative embodiment.

FIG. 2A shows a method in which the permeate collection tube 48 can be cleaned separated from the permeate circuit 23/24.

To this end the high-purity liquid of the membrane secondary side 12 is passed by means of the pump 27 via the circulation valve 66 and the permeate collection tube circulation line 68 over the cleaning devices 32 and/or 28 for such a long time until a microbiologically inactivating result has been achieved.

With this method the permeate circuit 23/24 or the permeate collection circuit 48/23/68 can be cleaned separately or together in a selective way.

The bypass valve 67 serves to discharge flawed permeate in the closed state of the permeate ring shut-off valve 35.

Figure 3A:
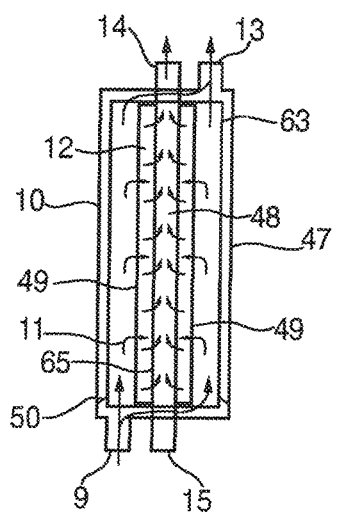
FIGS. 3A, 3B, and 4 show the scheme of associated devices.

FIG. 3A schematically shows a module (10) with inserted membrane module (63). The liquid is guided via the mixed-water connection (9) to the membrane primary circuit (11) and passes via the filter membrane (49) to the membrane secondary circuit (12). The permeate collection tube (48) is perforated (65) in such a manner that the liquid in the membrane primary circuit (11) which is supplied via the spirally arranged membrane pockets of the filter membrane (49) can enter into the permeate collection tube. It passes from there via the connections (14/15) into the high-purity distributor circuit. The concentrate is passed on via the connection (13).

Figure 3B:
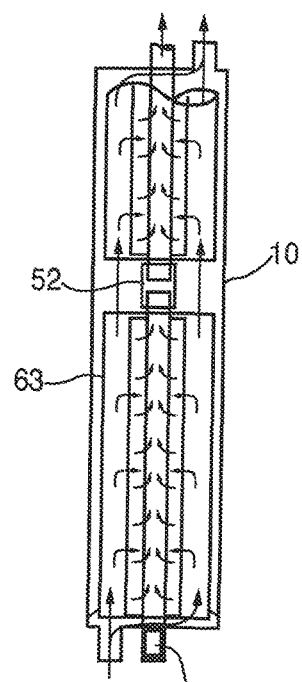

By comparison, FIG. 3B shows a 3-pole membrane according to the prior art. The liquid is here also supplied via the connection (9). The passage via the filter membrane (48) takes place as has already been described under 3A. Schematically shown is here the often employed technique of the series connection by means of the permeate collection tube connector (52) and the closure of the permeate side (51). The permeate collection tube can here be cleaned exclusively transmembranically.

Figure 4:
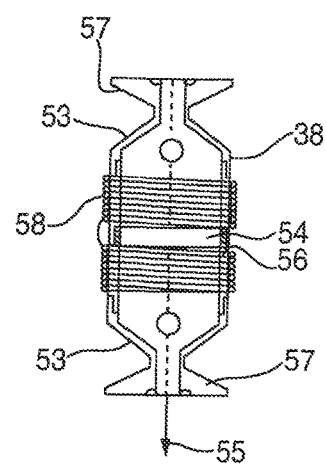

FIG. 4 shows the structure of a cleaning cell (38) with 3 electrodes, the middle electrode (54) being isolated spatially and electrically from the two outer electrodes (53). The liquid can here be introduced bidirectionally via the flow channel (55) into the cell. Due to the large surface distribution of the outer electrode (53) a uniform potential distribution is achieved in the inner electrode chamber. The isolating piece (56) serves as installation space for the middle electrode (54). The cup-shaped outer electrodes (53) have to be equipped with different connectors (57) such as e.g. clamp connection, plug nipple connection or hose connection.

The middle electrode (54) is inserted as an annular electrode body in the isolating piece (56).

Depending on the application, the material of the outer electrodes (53) consists of special steel, titanium, mixed titanium oxide or sintered carbon.

The middle electrode (54) consists of an oxidation-stable material such as e.g. conductive carbon, mixed titanium oxide, a ceramic mixture of metal oxides, titanium oxide or cobalt.

It is possible through the selection of the material and the electrical connection type to operate the cleaning chamber (38) as an electrolysis cell or as an electromagnetic cell or as a cell with electrode connections for current and voltage—also capacitively.

Preferably, a pole of the electrical supply is connected to the bridged outer electrodes (53), and the other pole to the middle electrode (54).

During operation of the cleaning chamber (38) as an electrolysis cell the two outer electrodes (53) are the cathodes, and the middle electrode (54) is the anode.

This electrolysis cell serves to produce oxygen radicals for the inactivation of the microorganisms or also to reduce lime scale.

FIG. 4 shows the design of a combined cleaning chamber (38) with 3 electrodes and a coil winding (51).

Decalcification is here carried out via the force lines of the coil-generated magnetic field in the liquid.

The use of Teflon-encapsulated ring magnets in the liquid or ring magnets outside the isolating piece (56) instead of the coil winding (51) is possible.

1. Feeding line
2. Measurement: input conductivity
3. Measurement: inflow
4. Water inlet valve
5. Supply tank
6. Level control
7. Pump
8. RS valve
9. Mixed water inflow
10. Filter module
11. Membrane primary circuit
12. Membrane secondary circuit
13. Concentrate outlet (line)
14. Permeate supply
15. Permeate circulation and bypass line
16. High-pressure throttle
17. Pressure-maintaining valve
18. Concentrate overflow
19. Concentrate discharge line
20. Concentrate discharge valve -continued 21. Concentrate flow meter
22. Drainage
23. Permeate feed line (can also be introduced into the consumer)
24. Permeate return line (can also be introduced into the consumer)
25. Connection point: consumer
26. Pressure maintaining valve - permeate return
27. Circulation pump
28. Ozone cell
29. Permeate ring - outflow valve
30. UV lamp
31. Temperature sensor
32. Heater
33. Temperature sensor
34. Conductivity cell
35. Permeate ring shut-off valve
36. Permeate ring safety valve
37. High-pressure throttle - bypass valve
38. Cleaning chamber
39. Heater - secondary side
40. Centrifugal chamber
41. Permeate ring - overflow valve
42. Interface line
43. Consumer - input valve
44. Consumer
45. Interface line - flushing valve
46. Throttle
47. Pressure pipe
48. Permeate collection tube
49. Filter membrane
50. Membrane seal
51. Plug - permeate collection tube
52. Connector - permeate collection tube
53. Outer electrodes
54. Middle electrode
55. Supplied liquid
56. Isolating piece
57. Connectors
58. Coil winding
59. RS valve
60. RO system
61. Circulation pump
62. RS valve
63. Membrane module
64. Cleaning sensor
65. Perforation - permeate collection tube
66. Circulation valve
67. Bypass valve
68. Permeate collector circulation line

The invention claimed is:

1. A method for sanitizing a reverse osmosis system to supply high-purity permeate, the method comprising:
supplying raw water to a feed tank and to a filter module using a raw-water inlet line having an inlet valve, the filter module comprising a semipermeable membrane and a permeate collection tube;
providing a primary circuit of the reverse osmosis system having a first pump connected to the filter module, wherein the semipermeable membrane is disposed within the primary circuit, the semipermeable membrane being coupled at a first end to a mixed-water connection of the primary circuit and at an opposed second end to a concentrate outlet line of the primary circuit, the primary circuit further comprising a bypass valve for modulating a pressure buildup in the reverse osmosis system;
providing a secondary circuit of the reverse osmosis system having a second pump and a heater, the second pump and heater being connected to the filter module, wherein the permeate collection tube is disposed within the secondary circuit, the permeate collection tube being coupled at a first end to a permeate circulation line of the secondary circuit and at an opposed second end to a permeate supply line of the secondary circuit;
separating the primary circuit from the secondary circuit using the semipermeable membrane disposed in the filter module, wherein the semipermeable membrane includes membrane pockets that are spirally arranged about the permeate collection tube such that liquid in the primary circuit which is supplied via the membrane pockets can enter into the permeate collection tube;
at least one of cleaning and disinfecting the secondary circuit of the reverse osmosis system while the raw-water inlet line is in a disconnected state and the inlet valve is in a closed state using the second pump and the heater;
wherein said at least one of cleaning and disinfecting comprises:
activating the second pump using computer-readable instructions with predetermined intervals and execution times;
activating the heater to heat permeate in the secondary circuit to a disinfecting temperature;
circulating the raw-water in the primary circuit using the first pump via the feed tank; and
opening the bypass valve for achieving a predetermined pressure in the secondary circuit and a predetermined flow velocity in the primary circuit.

2. The method of claim 1, further comprising separating the reverse osmosis system from a water network during a non-use period, and parking the reverse osmosis system without water connection at a different place.

3. The method of claim 1, further comprising performing the at least one of cleaning and disinfecting of the secondary circuit of the reverse osmosis system at a predetermined hygienic level for a predetermined period of time so that before operation no delay time is afforded.

4. The method of claim 1, wherein the computer-readable instructions are independently running preselectable computer-readable instructions.

5. The method of claim 1, wherein the disinfecting temperature is a predetermined temperature for disinfecting the high-purity permeate.

6. The method of claim 1, further comprising performing the at least one of cleaning and disinfecting of the secondary circuit of the reverse osmosis system without water consumption and without water waste.

7. The method of claim 1, further comprising flushing the membrane from deposits of a biofilm on a primary side of the membrane using the first pump so that no contaminants pass the membrane to a secondary side of the membrane.

8. The method of claim 1, further comprising:
supplying the high-purity permeate from the secondary circuit to a dialysis device coupled to the secondary circuit.

9. A method for sanitizing a reverse osmosis system to supply high-purity permeate, the method comprising:
supplying raw water to a feed tank and to a filter module using a raw-water inlet line having an inlet valve, the filter module comprising a semipermeable membrane and a permeate collection tube;
providing a primary circuit of the reverse osmosis system having a first pump connected to the filter module, wherein the semipermeable membrane is disposed within the primary circuit, the semipermeable membrane being coupled at a first end to a mixed-water connection of the primary circuit and at an opposed second end to a concentrate outlet line of the primary circuit, the primary circuit further comprising a bypass valve for modulating a pressure buildup in the reverse osmosis system;

providing a secondary circuit of the reverse osmosis system having a second pump and a heater, wherein the permeate collection tube is disposed within the secondary circuit, the permeate collection tube being coupled at a first end to a permeate circulation line of the secondary circuit and at an opposed second end to a permeate supply line of the secondary circuit, the permeate circulation line being connected to the second pump and the permeate supply line being connected to the heater;

separating the primary circuit from the secondary circuit using a semipermeable membrane disposed in the filter module, wherein the semipermeable membrane includes membrane pockets that are spirally arranged about the permeate collection tube such that liquid in the primary circuit which is supplied via the membrane pockets can enter into the permeate collection tube;

at least one of cleaning and disinfecting the secondary circuit of the reverse osmosis system while the raw-water inlet line is in a disconnected state and the inlet valve is in a closed state using the second pump and the heater;

wherein said at least one of cleaning and disinfecting comprises:

activating the second pump using computer-readable instructions with predetermined intervals and execution times;

activating the heater to heat permeate in the secondary circuit to a disinfecting temperature;

circulating the raw-water in the primary circuit using the first pump via the feed tank; and opening the bypass valve for achieving a predetermined pressure in the secondary circuit and a predetermined flow velocity in the primary circuit.

10. The method of claim 9, further comprising:

opening an outflow valve to connect the feed tank to the secondary circuit;

heating water in the secondary circuit using the heater;

circulating the heated water through the feed tank with the first pump to further clean the primary circuit and the secondary circuit of the reverse osmosis system.

11. The method of claim 10, wherein said circulating the heated water further uses the second pump to support circulation in the secondary circuit.

12. The method of claim 9, wherein, in the secondary circuit, a consumer line is disposed between the heater and the second pump.

* * * * *